(12) United States Patent
Yoshida et al.

(10) Patent No.: US 7,965,880 B2
(45) Date of Patent: Jun. 21, 2011

(54) LUMEN TRACKING IN COMPUTED TOMOGRAPHIC IMAGES

(75) Inventors: Hiroyuki Yoshida, Watertown, MA (US); Janne Nappi, Boston, MA (US); Michael E. Zalis, Newtonville, MA (US); Wenli Cai, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 12/832,306

(22) Filed: Jul. 8, 2010

(65) Prior Publication Data

US 2010/0278403 A1 Nov. 4, 2010

Related U.S. Application Data

(63) Continuation of application No. 11/607,623, filed on Nov. 30, 2006, now Pat. No. 7,809,177.

(60) Provisional application No. 60/741,103, filed on Nov. 30, 2005.

(51) Int. Cl.
*G06K 9/00* (2006.01)
*A61B 6/00* (2006.01)
(52) U.S. Cl. .................. 382/128; 378/4; 378/21
(58) Field of Classification Search .......... 382/128–134, 382/190; 600/407, 410, 411, 425, 427; 378/4, 378/8, 21–27, 98.4, 101, 901; 128/920, 922
See application file for complete search history.

(56) References Cited

U.S. PATENT DOCUMENTS

| | | | |
|---|---|---|---|
| 5,647,018 A * | 7/1997 | Benjamin | 382/128 |
| 5,920,319 A | 7/1999 | Vining et al. | |
| 6,331,116 B1 | 12/2001 | Kaufman et al. | |
| 6,343,936 B1 * | 2/2002 | Kaufman et al. | 434/262 |
| 6,366,800 B1 * | 4/2002 | Vining et al. | 600/425 |
| 7,226,410 B2 * | 6/2007 | Long | 600/114 |
| 7,596,256 B1 * | 9/2009 | Arie et al. | 382/131 |
| 2003/0095695 A1 | 5/2003 | Arnold | |
| 2004/0114790 A1 | 6/2004 | Yamamoto et al. | |
| 2004/0136584 A1 | 7/2004 | Acar et al. | |
| 2004/0167400 A1 | 8/2004 | Kaufman | |
| 2005/0152588 A1 | 7/2005 | Yoshida et al. | |
| 2006/0094961 A1 | 5/2006 | Mikheev et al. | |
| 2007/0116346 A1 | 5/2007 | Peterson et al. | |
| 2008/0055308 A1 | 3/2008 | Dekel et al. | |
| 2008/0273781 A1 | 11/2008 | Manduca et al. | |

FOREIGN PATENT DOCUMENTS

WO WO03034176 A2 4/2003

(Continued)

OTHER PUBLICATIONS

Cai, et al., Digital Bowel Cleansing for Computer-Aided Detection of Polyps in Fecal-Tagging CT Colonography, Proc. of SPIE 6144:61442-1-614422-9, Mar. 10, 2006.

(Continued)

*Primary Examiner* — Abolfazl Tabatabai
(74) *Attorney, Agent, or Firm* — Quarles & Brady LLP

(57) ABSTRACT

A lumen tracking method and system automatically extracts a colon from CT image data by locating landmarks in the image data, based on known anatomic features or other predictable features. If the colon is segmented, the method and system may use the landmarks to evaluate candidate segments for inclusion in the extracted colon.

19 Claims, 16 Drawing Sheets

FOREIGN PATENT DOCUMENTS

| WO | WO2004075117 A1 | 9/2004 |
|---|---|---|
| WO | WO2005101314 A2 | 10/2005 |

OTHER PUBLICATIONS

Chen, et al., A Novel Approach to Extract Colon Lumen from CT Images for Virtual Colonoscopy, IEEE Transactions on Medical Imaging, 19(12):1220-1226, Dec. 2000.

Chen, et al., Electronic Colon Cleansing by Colonic Material Tagging and Image Segmentation for Polyp Detection: Detection Model and Method Evaluation, Nuclear Science Symposium Conference Record, 3:18131-18135, Oct. 25, 2000.

Ciarlet, et al., Level Set Methods and Fast Marching Methods, Cambridge Mnographs on Applied and Computational Mathematics, Cambridge University Press, 2d Edition, ISBN 0521645573, (Front Matter Only), 1999.

Frimmel, et al., Fast and Robust Method to Compute Colon Centerline in CT Colonography, Proceedings of SPIE 5031:381-387, 2003.

Frimmel, et al., Centerline-Based Colon Segmentation for CT Colonography, Med. Phys. 32(8):2665-2672, Aug. 2005.

Lakare, et al., 3D Digital Cleansing Using Segmentation Rays, Proceedings Visualization, pp. 37-44, Oct. 8, 2000.

Nappi, et al., Automated Knowledge-Guided Segmentation of Colonic Walls for Computerized Detection of Polyps in CT Colonography, Journal of Computer Assisted Tomography, 26(4):493-504, 2002.

Nappi, et al., Region-Based Supine-Prone Correspondence for the Reduction of False-Positive CAD Polyp Candidates for CT Colonography, Academic Radiology 12(6):695-707, Jun. 2005.

Neubauer, Dissertation: Virtual Endoscopy for Preoperative Planning and Training of Endonasal Transsphenoidal Pituitary Surgery, TU Wien, May 2005.

Singh, et al., Automated 3D Segmentation of the Lung Airway Tree Using Gain-Based Region Growing Approach, MICCAI 2004, LNCS 3217, pp. 975-982, 2004.

Wan, et al., Automatic Centerline Extraction for Virtual Colonoscopy, IEEE Transactions on Medical Imaging 21(12):1450-1460, Dec. 2002.

Wang, et al., An Improved Electronic Colon Cleansing Method for Detection of Polyps by Virtual Colonoscopy, Proceedings of the 2005 IEEE Engineering in Medicine and Biology 27th Annual Conference, Shanghai, China, pp. 6512-6515, Sep. 1-4, 2005.

Zalis, et al., CT Colonography: Digital Subtraction Bowel Cleansing with Mucosal Reconstruction—Initial Observations, Radiology, 226(3):911-917, Mar. 2003.

Zalis, et al., Digital Subtraction Bowel Cleansing for CT Colonography Using Morphological and Linear Filtration Methods, IEEE Transactions on Medical Imaging 23(11):1335-1343, 2004.

International Search Report, PCT/US2006/046044, Apr. 5, 2007.

International Search Report, PCT/US2006/045789, Apr. 27, 2007.

International Search Report, PCT/US2006/045803, Apr. 27, 2007.

International Preliminary Report on Patentability, PCT/US2006/045789, Dec. 27, 2007.

International Preliminary Report on Patentability, PCT/US2006/045803, Jun. 3, 2008.

International Preliminary Report on Patentability, PCT/US2006/046044, Nov. 27, 2007.

Chapter II Demand, Article 34 Amendment, Response to Written Opinion, PCT/US2006/045789, Sep. 28, 2007.

Chapter II Demand, Article 34 Amendment, Response to Written Opinion, PCT/US2006/046044, Oct. 2, 2007.

United States Patent and Trademark Office, Office Action Summary and Detailed Action, U.S. Appl. No. 11/606,433, Mar. 10, 2010.

United States Patent and Trademark Office, Interview Summary, U.S. Appl. No. 11/606,433, Jun. 14, 2010.

United States Patent and Trademark Office, Office Action Summary and Detailed Action, U.S. Appl. No. 11/606,433, Jul. 28, 2010.

United States Patent and Trademark Office, Office Action Summary and Detailed Action, U.S. Appl. No. 11/606,433, Nov. 15, 2010.

United States Patent and Trademark Office, Office Action Summary and Detailed Action, U.S. Appl. No. 11/607,623, Jan. 12, 2010.

United States Patent and Trademark Office, Notice of Allowance, U.S. Appl. No. 11/607,623, Jul. 16, 2010.

United States Patent and Trademark Office, Office Action Summary and Detailed Action, U.S. Appl. No. 11/607,195, Mar. 10, 2010.

United States Patent and Trademark Office, Interview Summary, U.S. Appl. No. 11/607,195, Jun. 14, 2010.

United States Patent and Trademark Office, Notice of Allowance, U.S. Appl. No. 11/607,195, Sep. 28, 2010.

* cited by examiner

LUMEN TRACKING IN COMPUTED TOMOGRAPHIC IMAGES

CROSS REFERENCE TO RELATED APPLICATIONS

This application is a continuation of U.S. patent application Ser. No. 11/607,623, filed Nov. 30, 2006, titled "Lumen Tracking in Computed Tomographic Images," which claims the benefit of U.S. Provisional Patent Application No. 60/741,103, filed Nov. 30, 2005, titled "A Method for Computer-Aided Detection of Lesions in Radio-Opaque Contrast Materials," the entire contents of each of which are hereby incorporated by reference herein, for all purposes. This application is related to U.S. patent application Ser. No. 11/606,433, titled "Adaptive Density Correction in Computed Tomographic Images," filed on Nov. 30, 2006, and U.S. patent application Ser. No. 11/607,195, titled "Adaptive Density Mapping in Computed Tomographic Images," filed on Nov. 30, 2006.

STATEMENT REGARDING FEDERALLY SPONSORED RESEARCH OR DEVELOPMENT

This invention was made with Government support Grant Number CA095279 awarded by the National Cancer Institute. The U.S. Government has certain rights to the invention.

TECHNICAL FIELD

The present invention relates to computed tomography (CT) and, more particularly, to CT systems that track a lumen through possibly disconnected lumen segments to form a continuous lumen and extract lumen walls that define the lumen.

BACKGROUND ART

Colorectal cancer is one of the leading causes of cancer-related deaths. Patient screening can reduce colon cancer by facilitating early detection and removal of pre-cancerous polyps. Colonoscopy is considered to have the highest diagnostic performance for screening colon cancer; however, colonoscopy also has a high cost, risk of complications and incidents of patient non-compliance. A minimally invasive alternative procedure, called computed tomography colonography (CTC) or "virtual colonoscopy," is expected to be more cost effective and to involve a lower risk of complications than traditional colonoscopy.

Proper bowl preparation is considered essential for confident detection of colorectal lesions using CTC. This preparation traditionally includes cathartic cleansing of a patient's colon, because residual material in the colon reduces the sensitivity of CTC by imitating polyps. However, cathartic cleansing usually involves administering a laxative. Such cleansings are uncomfortable for the patient, and some residual material remains in the colon, even after such a cleansing. Orally-administered radio-opaque (or high X-ray opacity) contrast agents, such as dilute barium, can be used to opacify residual fluid and stool, so these opacified ("tagged") materials can be identified and distinguished from polyps or other soft tissues. Procedures that use such tagging are commonly referred to as "fecal tagging CTC" (ftCTC).

Interpreting a large number of ftCTC screening cases can be time-consuming for a radiologist, who may grow weary of the task and occasionally miss small polyps or even subtle cancers. Automated image processing ("computer-aided detection" (CAD)) tools can be used to rapidly point out suspicious lesions to radiologists. However, in ftCTC, automated image processing is complicated by an effect commonly known as pseudo-enhancement (PEH), which is an artifactual increase in the observed X-ray opacity (radio density) of tissues due to the presence of a near-by high radio density tagging agent.

In computed tomography (CT), the internals of an object, such as a human body, are imaged by taking X-ray measurements, yielding data that represents the object as many tightly packed cubes ("voxels"). The radio density of each voxel is calculated by taking the X-ray measurements through the object from a large number of perspectives. A computer digitally processes the X-ray measurements and generates data that represents a three-dimensional model of the object, including the internals of the object. Essentially, the computer "stacks" a series of "slices" of the object to create the model. The data can then be analyzed by a CAD tool. Alternatively or in addition, the data can be used to generate a three-dimensional display or for some other purpose.

The radio density (also called the "CT attenuation" or "CT number") of each voxel is represented by a numeric value along an arbitrary scale (the Hounsfield scale), in which −1,000 represents the radio density of air, and +1,000 represents the radio density of bone. Air causes very little X-ray attenuation and is typically depicted in black on X-ray films, in CT images, etc., whereas bone greatly attenuates X-rays and is typically depicted in white on these films and images. Fat has a radio density of about −120 Hounsfield Units (HU), and muscle has a radio density of about +40 HU. Water is defined as having a radio density of 0 (zero) HU.

Intermediate amounts of CT attenuation are usually depicted by shades of gray in CT images. Because the human eye is unable to distinguish among 2000 shades of grey (representing HU values between +1,000 and −1,000), a radiographer selects a range of CT attenuations that is of interest (i.e., a range of HU values, known as a "window"), and all the CT attenuations within this range are spread over an available gray scale, such as 256 shades of gray. This mapping of a range of CT attenuations to shades of gray is known as "windowing." The center of the range is known as the "window level." Materials having radio densities higher than the top of the window are depicted in white, whereas materials having radio densities lower than the bottom of the window are depicted in black.

Windowing facilitates distinguishing between tissues having similar radio densities. For example, to image an area of a body, such as the mediastinum or the abdomen, in which many tissues have similar radio densities, a narrow range of CT attenuations is selected, and these CT attenuations are spread over the available shades of gray. Consequently, two tissues with only a small difference between their radio densities are ascribed separate shades of gray and can, therefore, be differentiated.

CAD tools identify polyps of interest based on shape. These polyps occur on the inside wall of the colon. Thus, to facilitate automatic polyp identification, a CAD system should receive data representing an extracted colon, but not other structures (such as a small bowel or lung base), because polyps or polyp-like features in these other structures can lead to false positive (FP) diagnoses. To limit the structures that are considered by a CAD system, the colon (and no other structures) should be extracted from CT image data. Extracting the colon involves identifying a colonic lumen. A "lumen" is a space inside any tubular structure in a body, such as an intestine, artery or vein. Because polyps occur on the inside wall of the colon, the colonic lumen can be used to extract the colonic wall from the CT image data.

Unfortunately, a patient's colon may not be fully distended when the CT image data is collected. That is, portions of the colon may be collapsed or may be filled with tagged material. In this case, the CT image data may contain several, sometimes many, disconnected lumen-like structures, some of which may be undesirable to include in an extracted colon.

Thus, tagging and PEH present problems for the automated extraction of the colon, which is an important part of any automated CAD scheme for CTC. Even if tagging is not used, fully automated colon extraction is a challenging problem in cases where the colonic lumen is split into multiple disconnected components, some of which may be separated from each other in distance by collapsed regions. Although visible regions of a colonic lumen can be reconnected over the collapsed segments of the colon, pieces of small bowel could be inadvertently included in the extracted region.

The presence of tagging can further complicate colon extraction, because thin walls between the colon and small bowel may become invisible in the ftCTC data due to PEH, which can result in complex networks of interconnected lumen paths between the colon and small bowel. In ftCTC, the colon is also more often connected to the small bowel through an open ileocecal valve than in CTC without tagging, because the opacified fluid at the ileocecal valve facilitates tracking the colonic lumen directly into the small bowel. Furthermore, osseous structures and tagged materials have similar CT attenuation values in ftCTC, and differentiating these materials may be challenging in cases where tagged regions and osseous structures appear to be directly connected because of a partial-volume effect and PEH.

SUMMARY OF EMBODIMENTS

An embodiment of the present invention provides a method for extracting a colon from computed tomographic image data. The method includes identifying a lumenic structure in the image data, such that the lumenic structure includes a landmark that represents an identified portion of the colon. The method also includes testing at least one lumenic structure that does not include a landmark that represents an identified portion of the colon for appropriateness to be appended to the identified lumenic structure. If the tested lumenic structure is appropriate, the method appends the tested lumenic structure to the identified structure.

The landmark may, for example, represent a rectum, a descending colon, a splenic flexure, a hepatic flexure, an ascending colon or a cecum.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

The contents of U.S. Provisional Patent Application No. 60/741,103, filed Nov. 30, 2005, titled "A Method for Computer-Aided Detection of Lesions in Radio-Opaque Contrast Materials," is hereby incorporated by reference herein.

In accordance with the present invention, a method and system for extracting a colon from CT image data locates landmarks in the image data, based on known anatomic features or other predictable features. If the colon is segmented, the method and system may use the landmarks to evaluate candidate segments for inclusion in the extracted colon.

Figure 1:
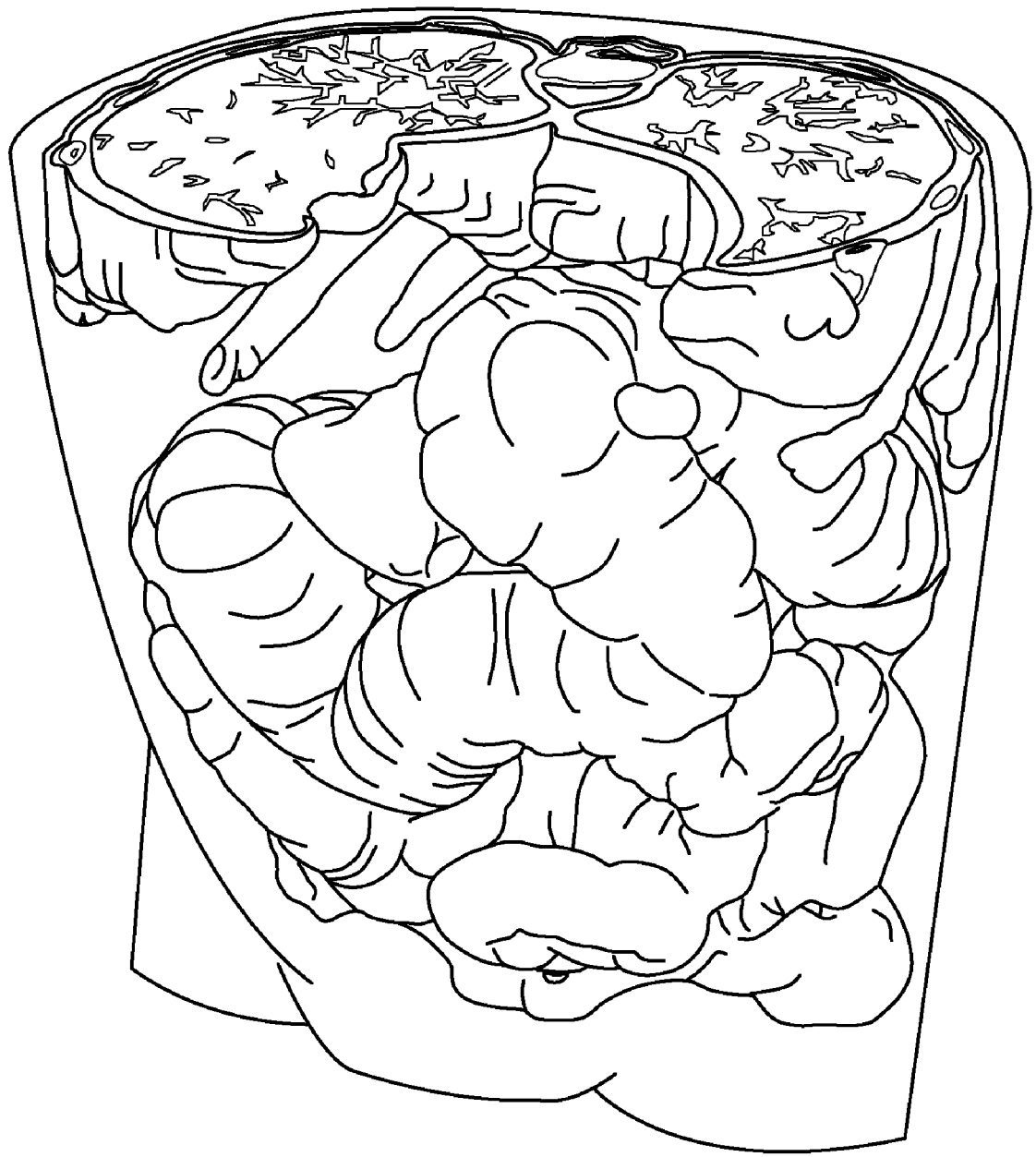
FIG. 1 is a 3-dimensional visualization of exemplary computed tomographic image data.
Figure 2:
FIG. 2 illustrates portions of the CT image data of FIG. 1.
Figure 2:
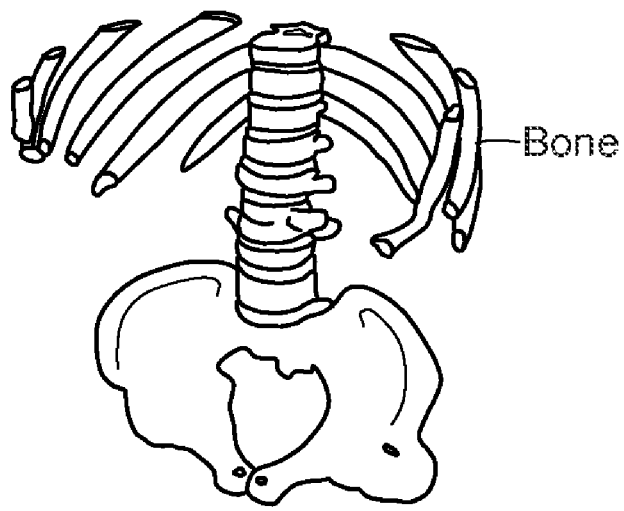
Figure 2:
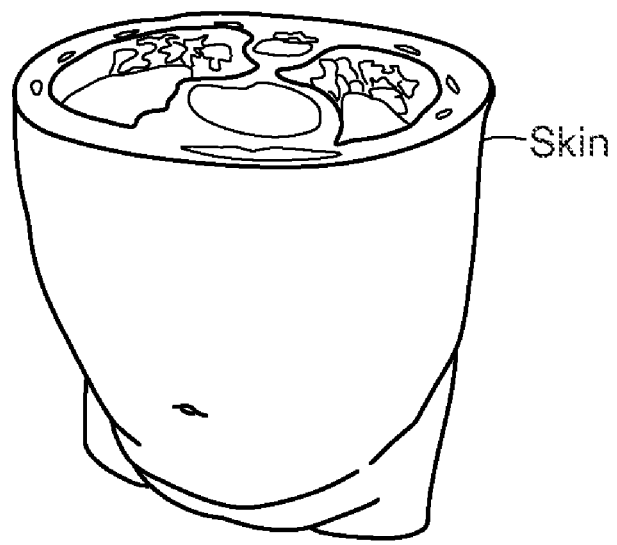

As noted, extracting an entire colon from CT image data is useful in automated polyp detection using CAD tools; however, portions of the colon may be collapsed, which complicates extracting the colon, without including other structures. As shown in FIG. 1, initial CT image data that include a colon typically also include other structures, such as skin, a lung base and bone. FIG. 2 illustrates portions of the CT image data, such as the lung base, bone and skin, which should be differentiated from the colon. Using conventional techniques, some of these structures can be differentiated from the colon. For example, bone can be identified by its CT attenuation, which is higher than the CT attenuations of the soft tissues of the colon.

Even using known techniques, the remaining CT image data may include structures that are undesirable for CTC and polyp detection. For example, the incidence of cancerous polyps in the lower bowel is quite small, even though the lower bowel may contain polyps or other features that have polyp-like shapes. Furthermore, the lungs and other non-colonic structures may include features having shapes that may be falsely detected as polyps by CAD tools. Thus, to reduce false positive (FP) detections by the CAD tools, it is desirable to exclude the lower bowel and other non-colonic structures before extracting the colon for analysis by the CAD tools.

Figure 3:
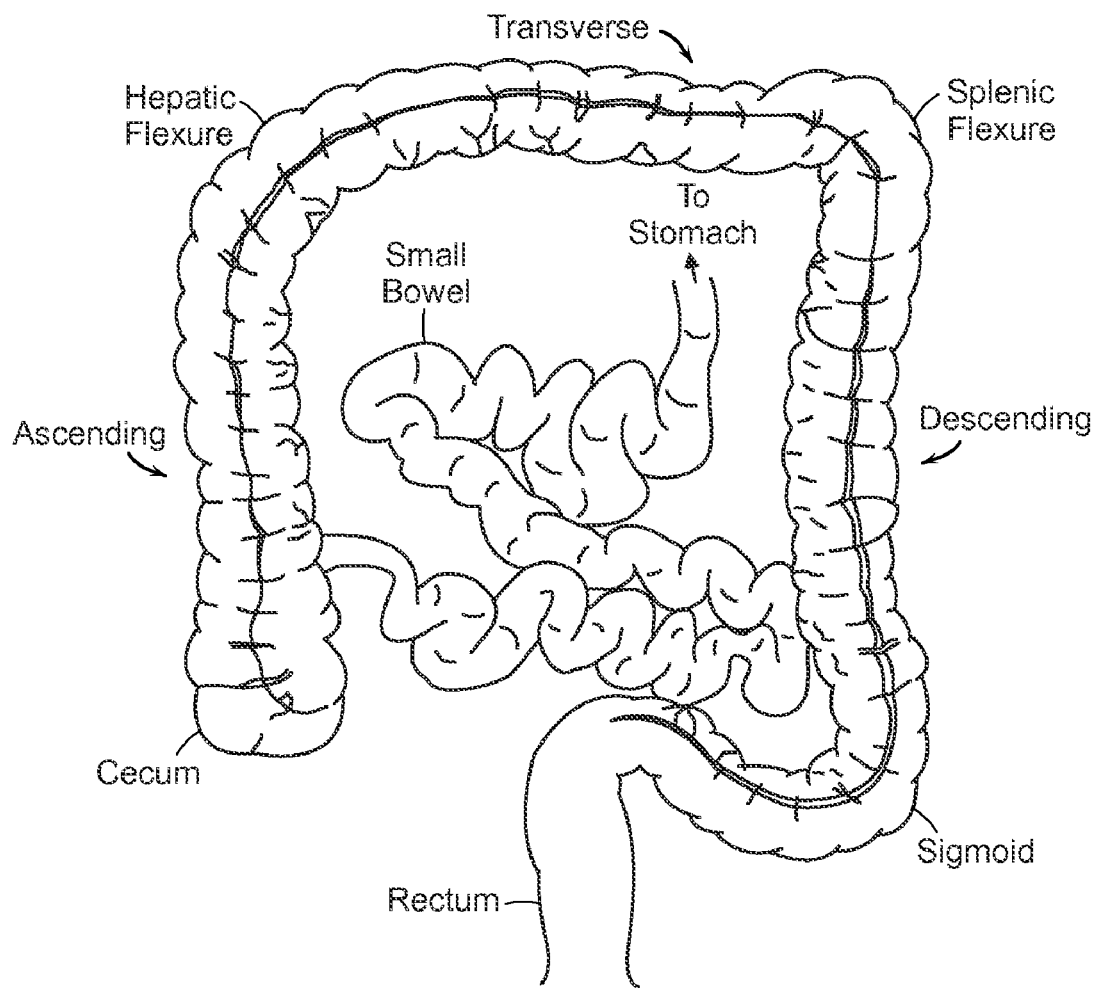
FIG. 3 is an annotated schematic diagram of a colon, including a small bowel.

As noted, sometimes the colon is segmented in the CT image data, which complicates extracting the colon without including these other structures. One embodiment of the present invention uses easily located points ("landmarks") on a colon to facilitate identifying a track through the colon and/or to identify portions of the colon in CT image data. The track need not lie along a centerline of the colon. FIG. 3 is an annotated schematic diagram of a colon, including a small bowel. The annotations identify several portions of the colon, such as the ascending bowel, hepatic flexure, splenic flexure, descending bowel, sigmoid and rectum.

Landmarks can be identified in CT image data by searching for various expected anatomical features and characteristics, such as location (absolute or relative to other structures), shape, size (absolute or relative to other structures), volume and/or proximity or connection to other known or identifiable structures. Other "hints" can be used to identify or increase the confidence in having located a landmark. Such hints can include expected CT attenuation, expected ratio of CT attenuation to that of adjacent structures, etc.

Figure 4:
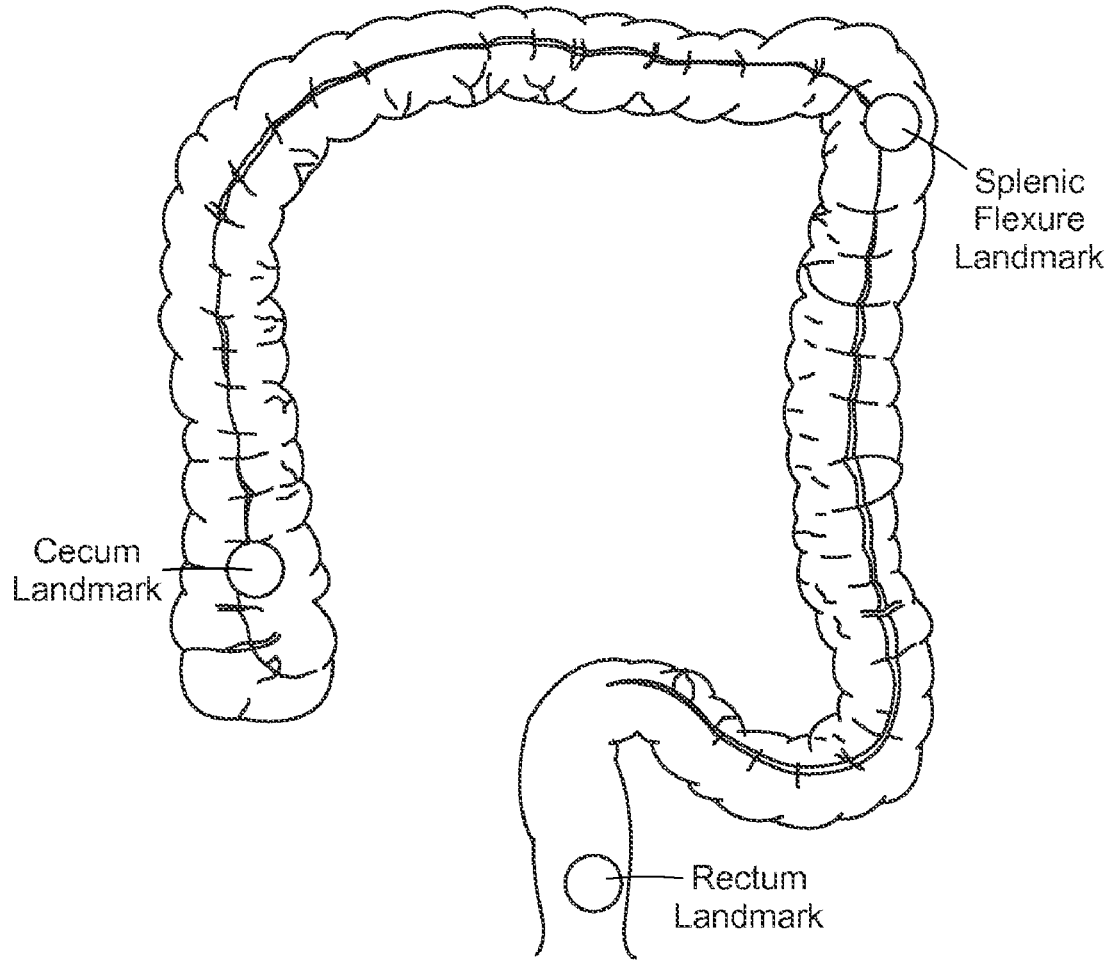
FIG. 4 is a schematic diagram of a colon with three exemplary landmarks identified, according to one embodiment of the present invention.

For example, the anus (not shown) can be identified, because of its location at the bottom center of the body. The rectum is known to be connected to the anus; thus, a lumen-like structure connected to the anus can be assumed to be the rectum. The descending bowel can be identified, because the descending bowel is known to be on the right side of a body (as viewed in FIG. 3) and the descending bowel is connected to the splenic flexure, which has a characteristic curve near the top of the descending bowel. The splenic flexure can be identified by its characteristic curve; thus, the splenic flexure can be used as a landmark. Similarly, the hepatic flexure is known to be located on the left side of the body, and it has a characteristic shape. Thus, the hepatic flexure can also be used as a landmark. Other landmarks can be identified by using known or predictable anatomic characteristics. FIG. 4 is a schematic diagram of a colon with three exemplary landmarks identified.

Figure 5:
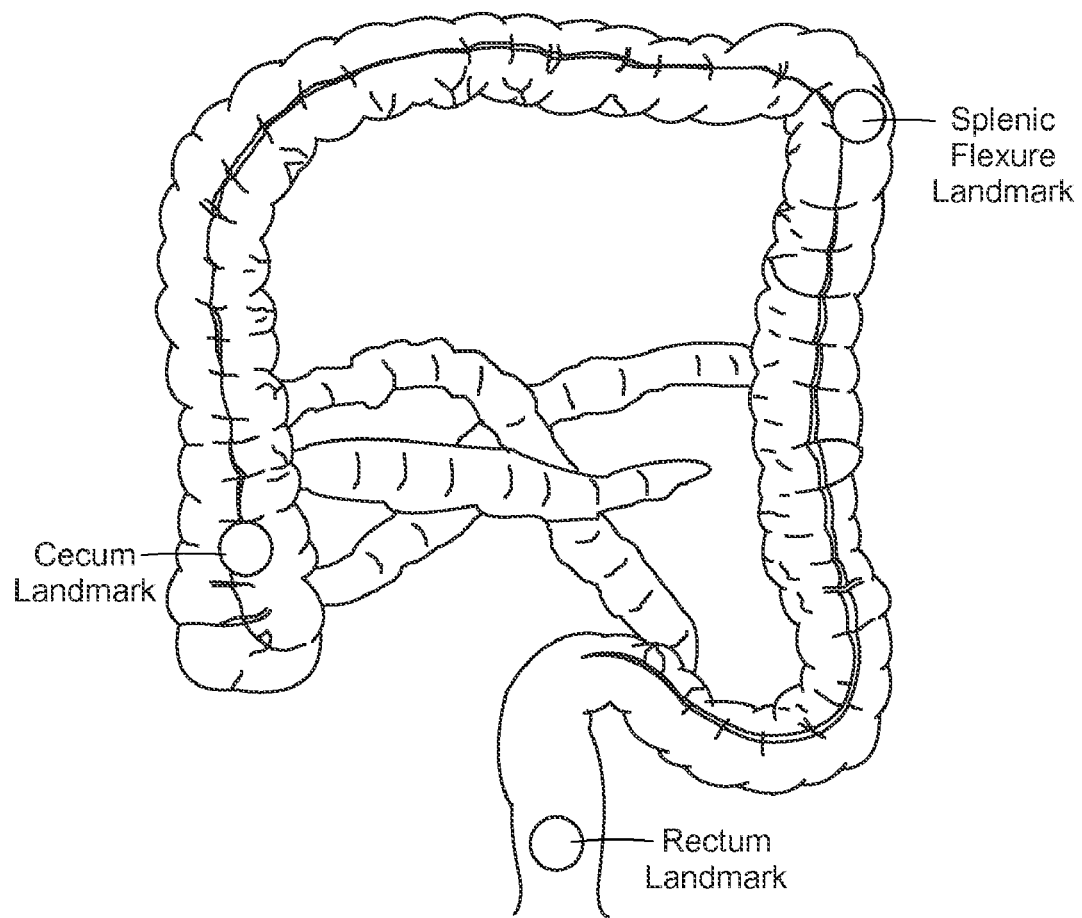
FIG. 5 is an exemplary CT image that includes a colon and several non-colon, lumen-like structures.

Landmarks can be used to distinguish a colonic lumen from other lumen-like structures. For example, for "fly-through" visualizations of the colon, colonic landmarks can be used to ensure the fly-through occurs through only the colon, and not the small bowel, stomach or other structures. FIG. 5 is an exemplary CT image that includes a colon and several non-colon, lumenic (lumen-like) structures. Locating one or more landmarks on the colon, then flying through only lumen(s) that include the landmarks ensures that the fly-through does not include non-colonic structures.

Landmarks can also be used to connect disconnected colonic segments. If a colon is segmented, such as because portions of the colon are collapsed, landmarks can be used to identify which lumen-like segments (or lumen tracks) in CT image data are definitely parts of the colon and which segments (or lumen tracks) are merely candidates for inclusion in a reconstructed colon (or colon lumen track). For example, once one or more segments of the colon are identified by the landmarks, candidates from a collection of unidentified segments can be tested to determine which one(s) should be included in a colon lumen track. Ideally, after segments are added to the identified colonic segments, the resulting colonic lumen track extends continuously, along a length of interest, from one end (such as the rectum) to the opposite end (such as the cecum).

Selection criteria are used to select from among several candidate segments to be connected to identified segments of the colon. For example, a candidate segment whose end is closest to the end of the identified colonic segment may be chosen. Alternatively, a candidate segment that extends in an expected direction from the end of the identified colonic segment may be chosen. Other selection criteria include using the longest candidate segment or using a candidate segment whose opposite end is closest to another identified segment of the colon, thus best "filling the gap" between the two identified segments. These and other criteria can be combined, such as by weighting each criterion and selecting the segment having the highest overall score. Optionally, if no appropriate candidate segment(s) can be selected, all the segments are concatenated, although this may include undesirable structures, such as the small bowel. Segment selection is described in more detail below.

In one embodiment of the present invention, the tracks of all lumen-like structures (or at least lumen-like structures that satisfy some pre-selection criteria) are determined Once these tracks are determined, the tracks having points that correspond to the locations of landmarks (such as within a predetermined distance) are selected as being within the colon. (The tracks can be determined before, during or after the landmarks are identified.) Once the colonic lumen sections are determined, other segments can be added to connect the disconnected colon, at least to the extent possible.

In another embodiment, lumen-like structures that include the landmarks are determined first (thus identifying portions of the colon), and then tracks of these lumens are determined These tracks can then be extended by adding other segments or by region growing to, ideally, connect the disconnected colon, at least to the extent possible. Region growing may involve starting at a point on a track of a lumen and testing voxels at progressively larger distances away from the track, such as voxels that are located along a radius away from the point on the track, until an interface with a soft tissue is encountered. Presumably, this interface is a colonic wall, particularly if tagged stool has been mapped to air or another gas. The distance away from the lumen track may be limited by a threshold value, such as a distance somewhat larger than the expected radius or diameter of the colon. The search need not be radially away from the lumen track. For example, the search may extend at an angle oriented somewhat toward the direction where the colon is expected to extend.

The methods and systems described herein may be used alone or in any combination. Furthermore, the methods and system described herein may be used to extract any type of lumen, lumen track or structure that defines a lumen, not just colonic lumens. For example, these methods and systems are equally applicable to blood vessels, lymph vessels and the like.

Colonic Lumen Tracking (CLT)

To extract the region of colon from CTC data for the detection of polyps, the abdominal region is first extracted automatically by use of a series of thresholding, morphological, and region-growing operations. Preferably, although not necessarily, the ftCTC data have been preprocessed by adaptive density correction (ADC) and adaptive density mapping (ADM) methods. Suitable ADC and ADM methods and systems are described in co-pending, commonly-assigned U.S. patent application Ser. No. [to be supplied], titled "Adaptive Density Correction in Computed Tomographic Images," filed on Nov. 30, 2006, and co-pending, commonly-assigned U.S. patent application Ser. No. [to be supplied], titled "Adaptive Density Mapping in Computed Tomographic Images," filed on Nov. 30, 2006, the contents of which are incorporated by reference herein.

The regions of soft tissue, tagging, and air are determined as described in the above-referenced patent applications. In particular, the colonic lumen is included in the region $L=A \cup T \cup A \backslash T$, which may also include extra-colonic structures such as small bowel or stomach. To identify the precise region of the colonic lumen in L, a path is calculated automatically through the colonic lumen in L as described below. The calculated path is similar to a colon centerline, except that it does not need to be precisely centered in the lumen. The regions of the colonic lumen and colonic wall are then extracted automatically by use of region growing from the calculated path.

Let $P=\{P_i\}(i=1, \ldots, n)$ denote a set of n paths for the n connected components of L, where the paths have been calculated automatically by use of a distance transform on the region L. Three landmarks are established automatically by use of a rule-based method: $L_r$ (rectum), $L_d$ (descending colon), and $L_c$ (cecum). If there exists a path $P_{rdc}$ that connects $L_r$ to $L_d$ and $L_d$ to $L_c$, in this order, then $P_{rdc}$ is considered as representing a complete colonic path, and any other paths in P are deleted.

Figure 6:
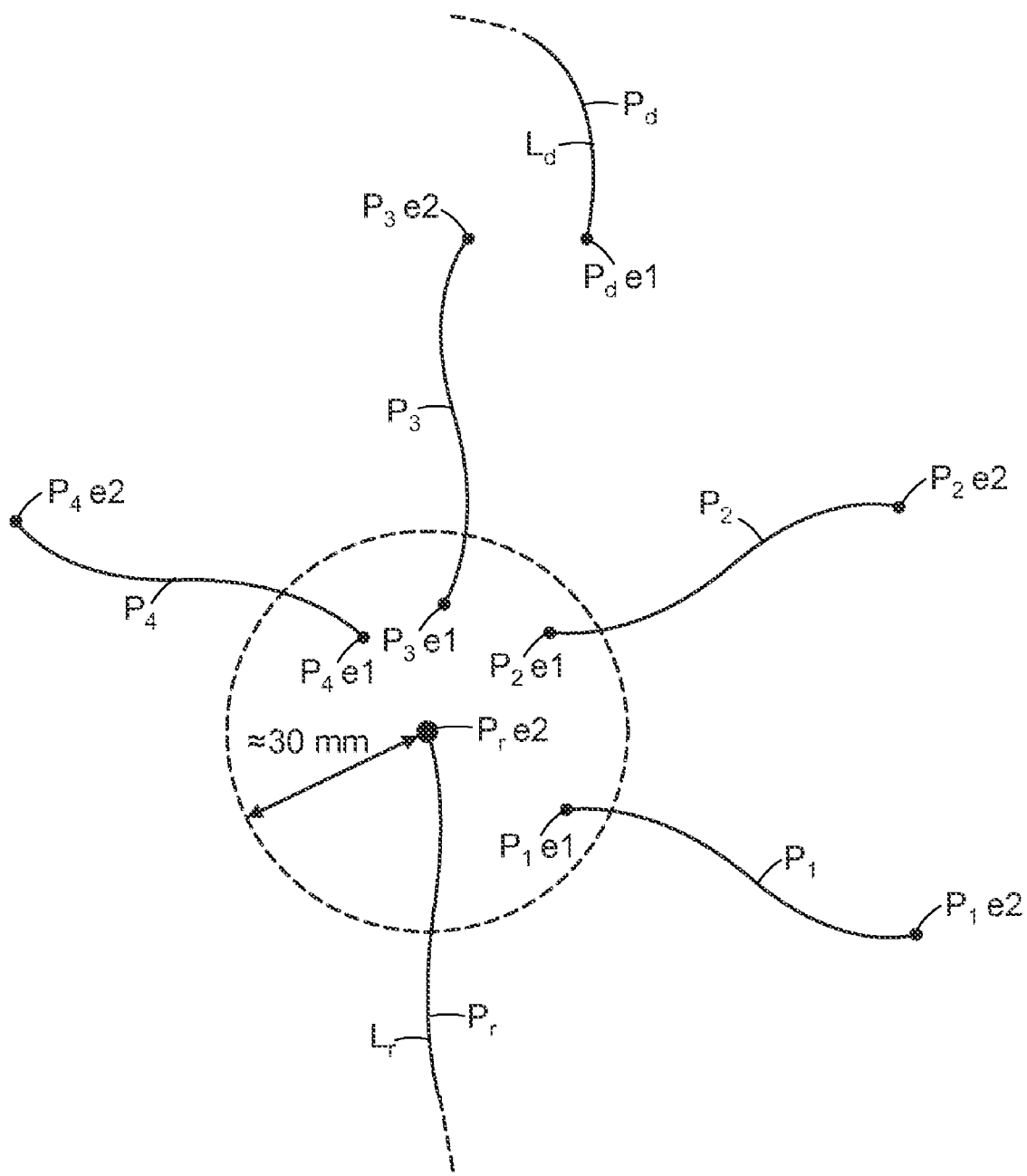
FIG. 6 is a schematic diagram of exemplary lumen tracks during a search for a segment to append to an existing segment, in accordance with one embodiment of the present invention.

If a single complete colonic path, $P_{rdc}$, was not found, this indicates that the colonic lumen is collapsed at one or more regions. To reconnect the disconnected lumen paths automatically into a complete path over collapsed regions, we first determine the paths $P_r$, $P_d$ and $P_c$ which include $L_r$, $L_d$, and $L_c$, respectively. As shown in FIG. 6, suppose that $P_r \neq P_d$ (the case of $P_c \neq P_d$ is calculated similarly). Let $P_r^{e2}$ represent the endpoint of the rectal segment $P_r$ which is closer to $L_d$, and let $P_d^{e1}$ represent the endpoint of the descending colon segment $P_d$ which is closer to $L_r$. Let $P_j^{e1}(j=1, \ldots, m)$ represent the endpoints of m candidate paths $P_j \notin \{P_r, P_d, P_c\}$ within a predetermined distance $N_c$, such as 30 mm, from $P_r^{e2}$, and let $P_j^{e2}(j=1, \ldots, m)$ represent the other endpoint of such paths $P_j$. If $D(P_r^{e2}, P_d^{e1}) \leq N_c$, where $D(a, b)$ is Euclidean distance between a and b, then $P_r^{e2}$ and $P_d^{e1}$ will be connected and $P_r = P_d$. Otherwise, the rectal segment $P_r$ will be connected to a candidate path $P_k$ which, for all $k \neq 1$, satisfies both of the following conditions:

$$D(P_r^{e2}, P_k^{e1}) + D(P_k^{e2}, P_d^{e1}) < D(P_r^{e2}, P_l^{e1}) + D(P_l^{e2}, P_d^{e1}) \quad (1)$$

and $$D(P_k^{e2}, P_d^{e1}) < D(P_r^{e2}, P_d^{e1}). \quad (2)$$

If the new connected path does not include $P_d$, the above step is repeated by choosing $P_k^{e2}$ as the new endpoint $P_r^{e2}$ of the new $P_r$, and by searching for new suitable endpoints within $N_c$ mm of the new $P_r^{e2}$.

If the above method fails to determine a single connected path which would connect the landmarks $L_r$, $L_d$, and $L_c$, in this order, then the set of all calculated paths in L, i.e., P, is used as the final lumen path This ensures that all colonic regions will be examined during the polyp detection step.

If a single connected path $P_{rdc}$ was established, the location of the ileocecal valve ($L_{icv}$) will be checked automatically to prevent the path from entering the small bowel through an open valve. Let $D(L_c)$ denote the value of distance transform (which is used to characterize lumen distension) at the location of the cecum landmark $L_c$. In most cases, $D(L_c) \gg D(L_{icv})$. First, $P_{rdc}$ is tracked from $L_c$ to a point $p_0$ where $D(p_0) < \frac{1}{2}D(L_c)$. This indicates that the lumen is narrowing. Next, we continue tracking the path from $p_0$ while comparing the distension between two successive points $D(p_i)$ and $D(p_{i+1})$. If $D(p_{i+1}) > D(p_i)$, then the lumen is expected to be widening at $p_{i+1}$ because of entering the small bowel. Therefore, the colon path is terminated at $p_i = L_{icv}$.

The region-growing step for extracting the colonic lumen from the calculated path is performed in two steps to minimize any potential leakage into the small bowel or stomach. First, the lumen path $P_{rdc}$ is used as a seed for a fast-marching region-growing method, where the growing region is not allowed to expand closer than d mm to the colonic wall. This constraint on the grown region prevents leakage from the lumen path to structures outside the colon. Next, the region-growing continues not only from the colon path $P_{rdc}$, but also from extra-colonic paths $\{P, P_{rdc}\}$. Whereas the former grown region will represent the colonic lumen, the latter grown region is simply used for preventing the former region from leaking into the small bowel or stomach, and it will be excluded from the final extracted region.

FIG. 7 illustrates steps of the CLT method. FIG. 7a shows the stacking of the input CT images into a volume, and FIG. 7b shows the labeling of the abdominal voxels. In FIG. 7c shows cut-plane views of the conversion of the CT volume into binary volume. The top of FIG. 7c shows a cut-plane view of a colon segment with air and tagged fluid. The middle of FIG. 7c shows the labeling of the segment: soft tissue is indicated by dark gray color, tagged fluid is indicated by white color, air is labeled by gray color, and the interface between the air and tagged fluid is indicated by light gray color. The bottom of FIG. 7c demonstrates how the binary conversion of the labels of air, tagged fluid, and their separating interface facilitates uniform tracking of the lumen. In FIG. 7d is a visualization of a piece of tracked path entering and exiting tagged fluid within the colonic lumen. The top of FIG. 7d shows an endoscopic view of a tracked lumen path entering and exiting tagged fluid, and bottom figure shows a cut-plane view of the same region, where the tracked path has been projected onto the image. FIG. 7e shows all tracked abdominal lumen paths.

Figure 7A:
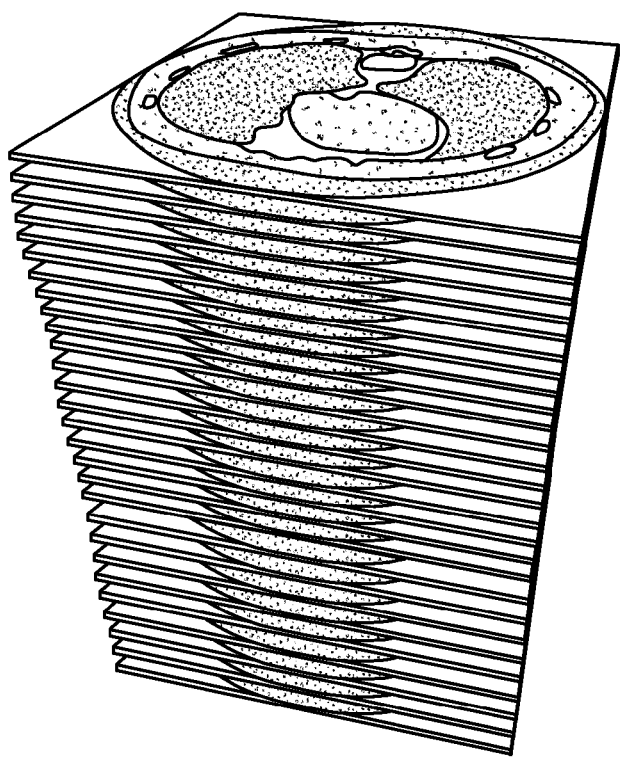
FIG. 7 illustrates steps of lumen tracking, in accordance with one embodiment of the present invention.
Figure 7B:
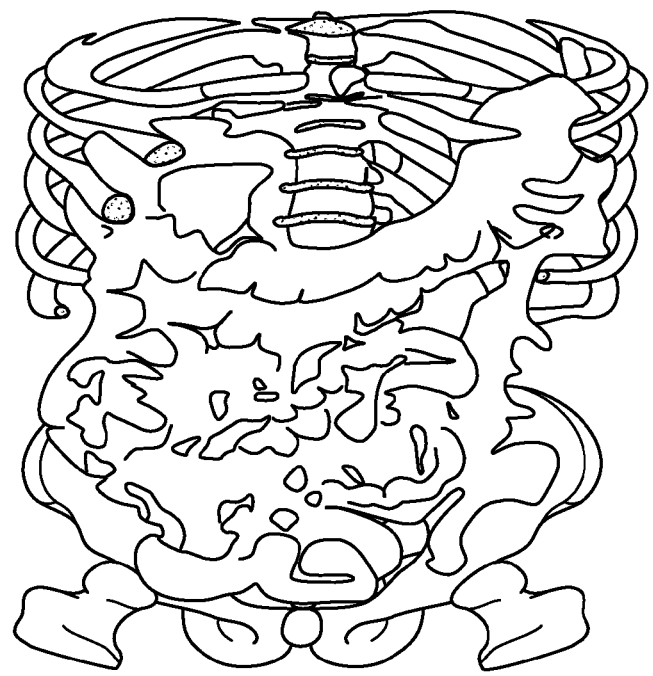
Figure 7C:
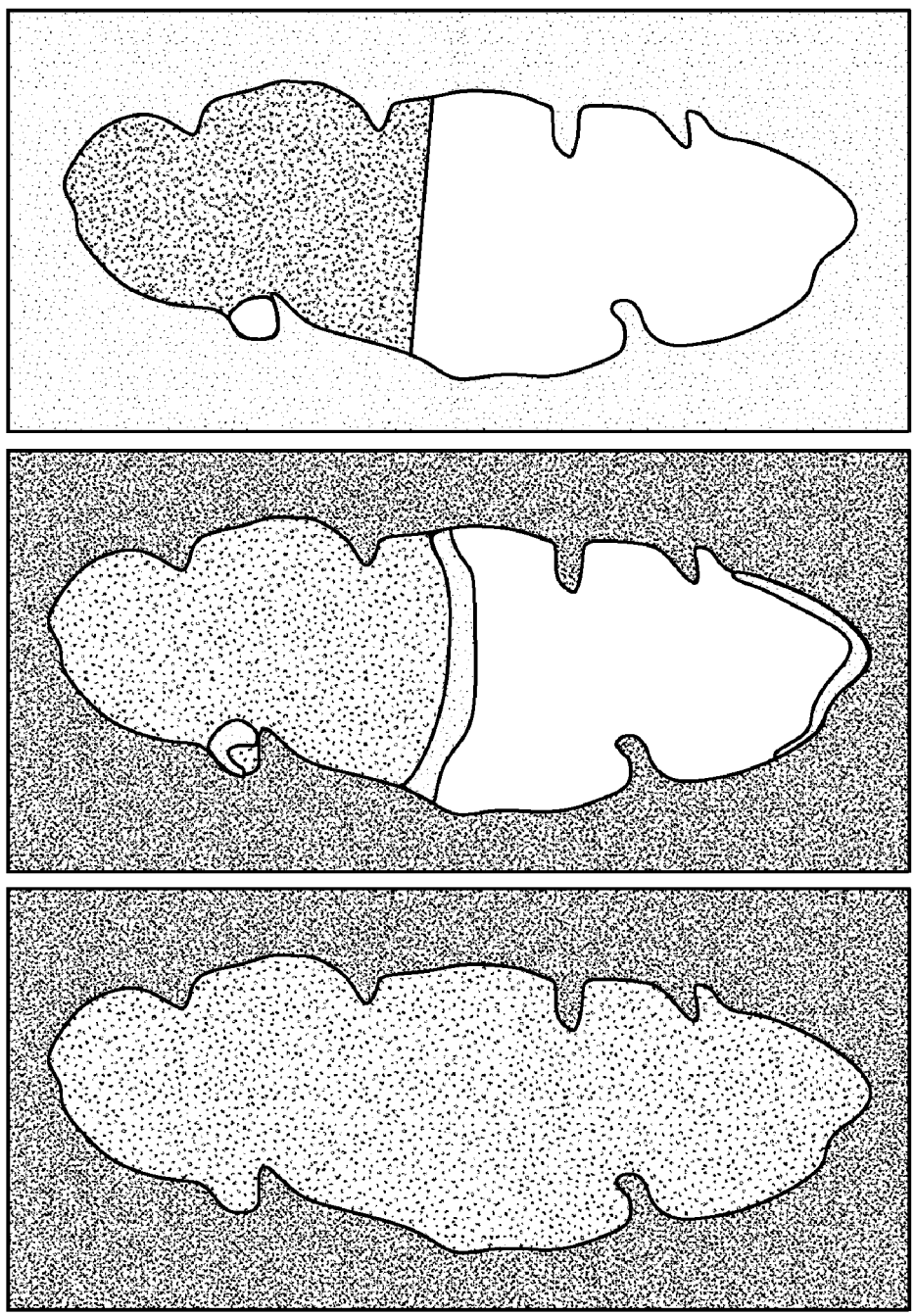
Figure 7D:
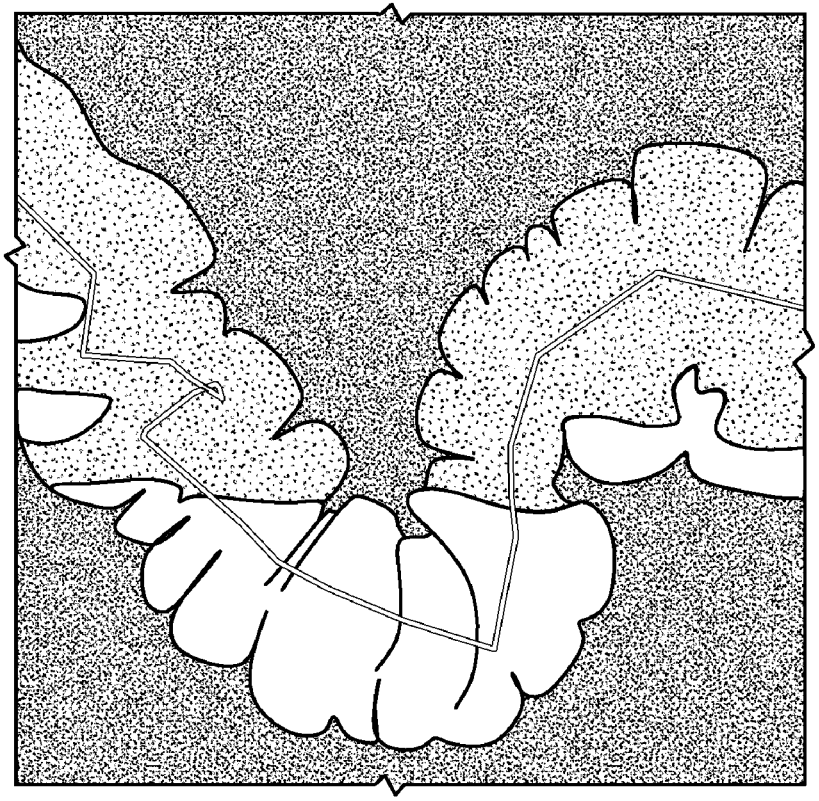
Figure 7D:
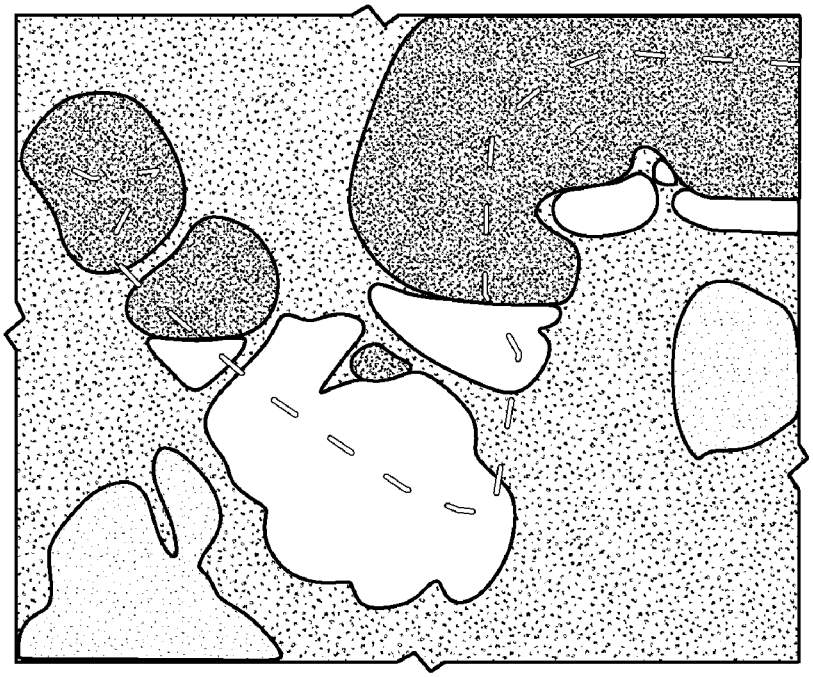
Figure 7E:
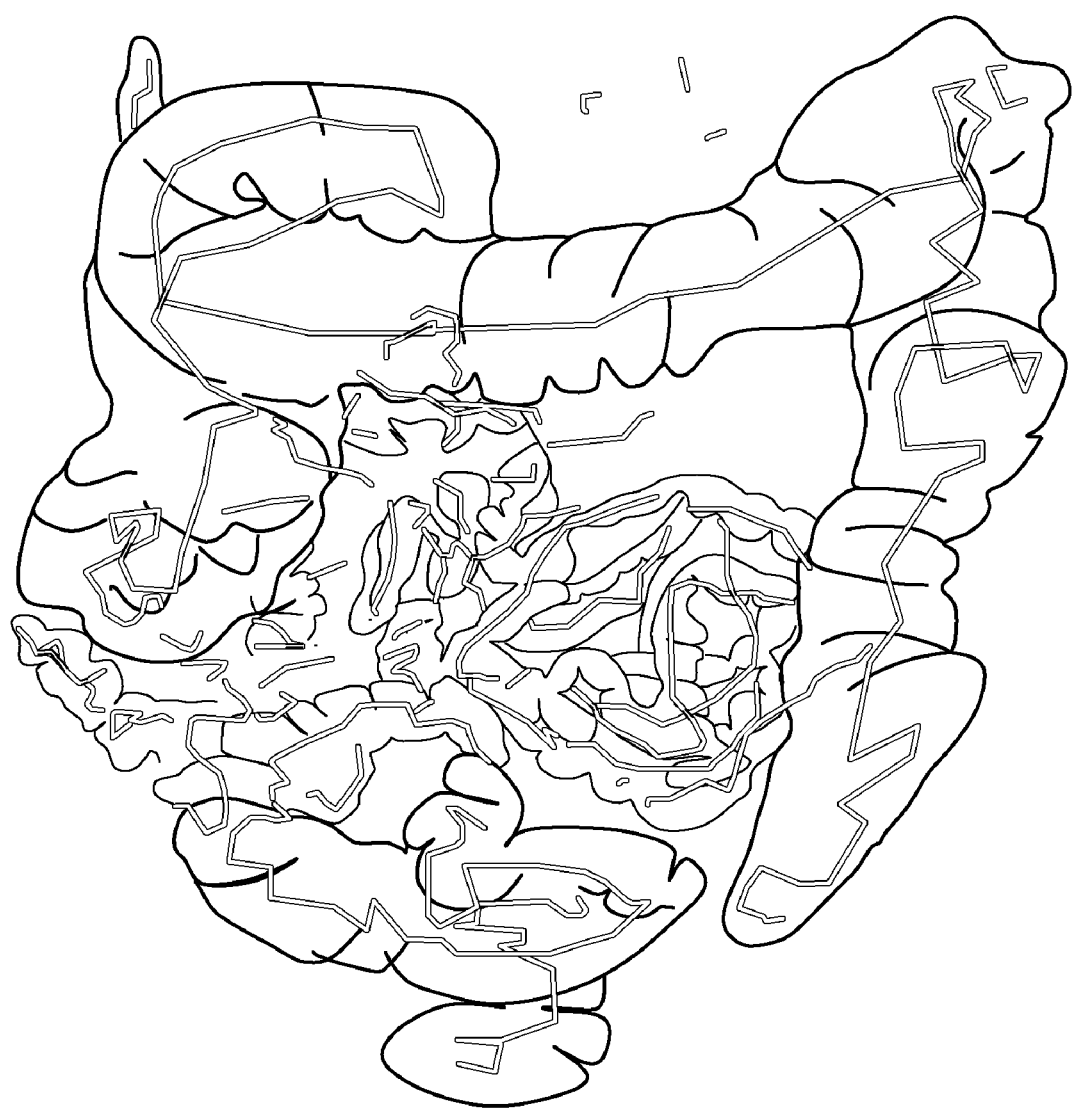
Figure 7F:
Figure 7G:
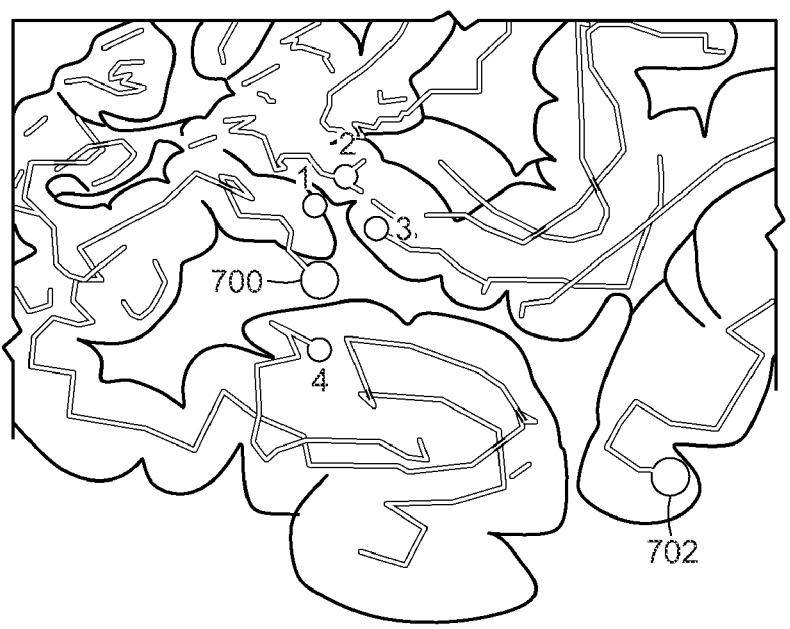
Figure 7H:
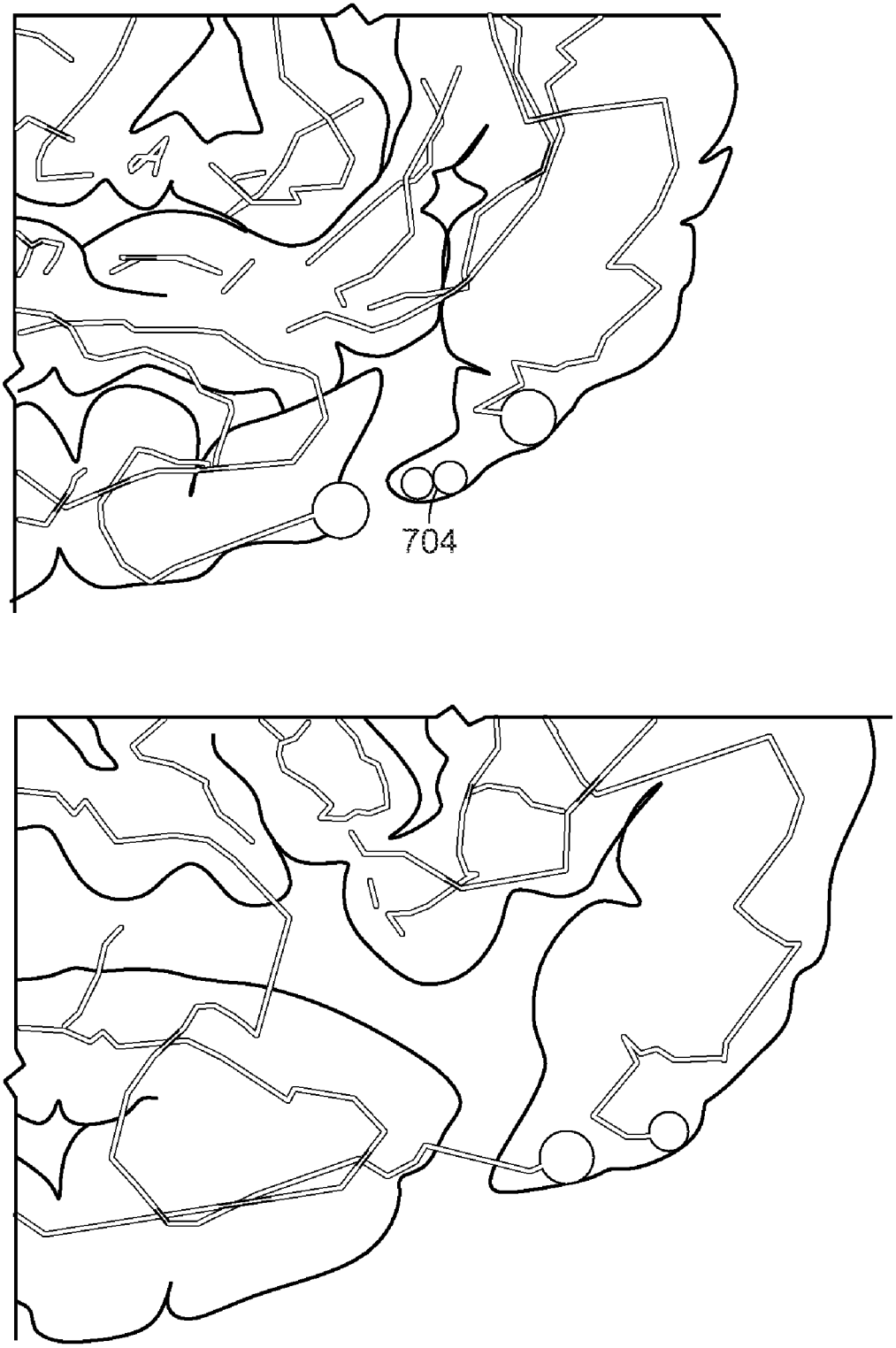
Figure 7I:
Figure 7J:
Figure 7K:
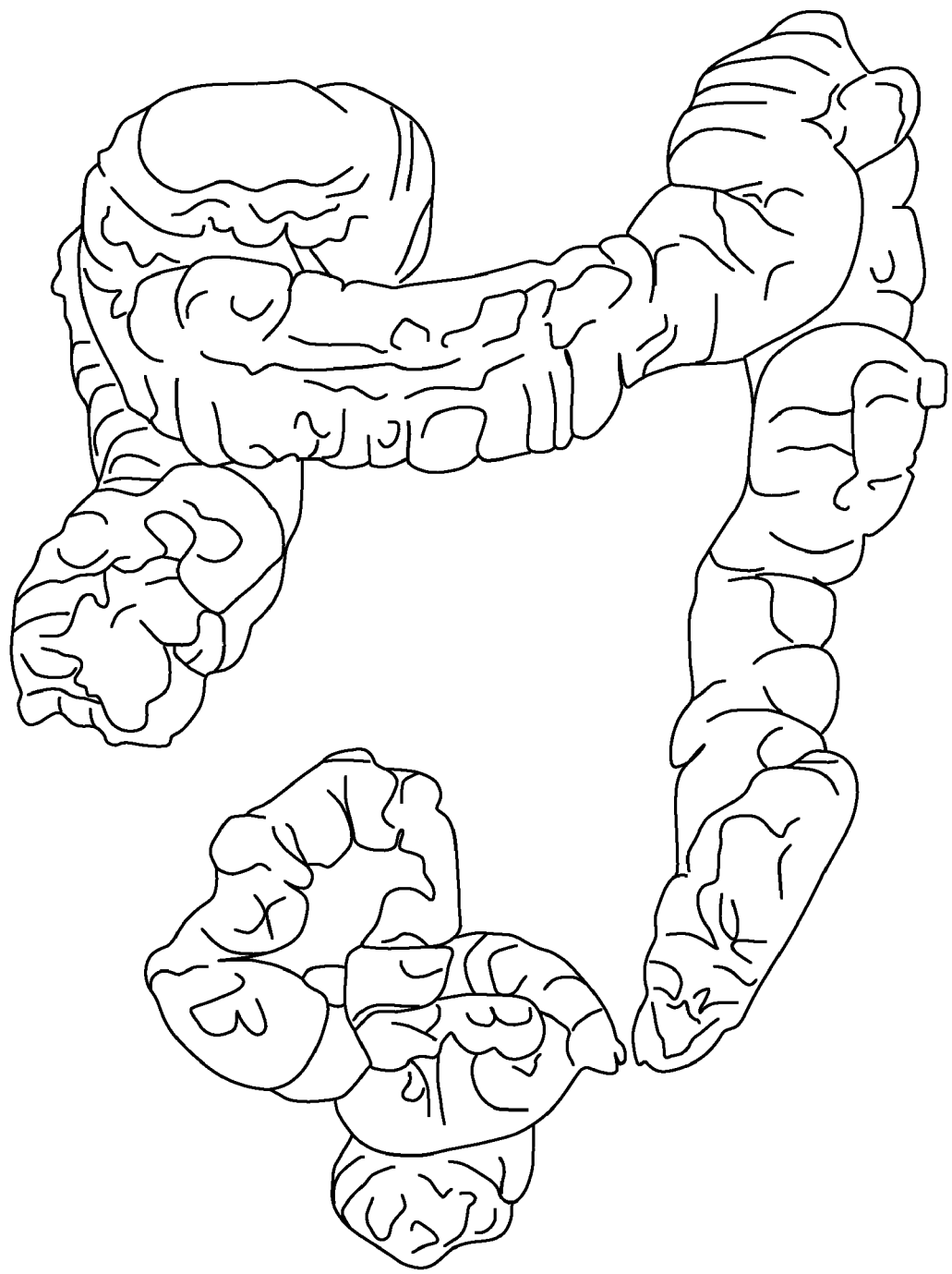

FIG. 7f shows the initially established landmarks (1=cecum (ascending colon), 2=descending colon, 3=rectum) and the primary colon segments tracked from these landmarks. Because the sigmoid colon is poorly distended and partially collapsed, there is no pathway from the rectal segment to the descending colon segment. FIG. 7g demonstrates the first step of the reconstruction of a complete lumen path. The large white sphere 700 indicates an endpoint of the rectal segment, and the large sphere 702 indicates an endpoint of the descending segment. The rectal endpoint 700 can be connected to four nearby endpoints, labeled 1-4 in the image, of which endpoint 4 will be chosen by the application of Eqs. (1) and (2). FIG. 4h shows how the tracking continues with the new rectal segment. In the top of the figure, a short isolated colonic segment 704 provides both candidate points for the next connection of the rectal segment. In the bottom of the figure, the endpoints of the rectal and descending segment are now close enough to be connected directly. In FIG. 7i, the final path is shown with adjusted landmark locations. In particular, the location of the landmark at cecum has been adjusted as explained earlier in this Section. FIG. 7j shows the result of the region-growing steps. The extracted lumen can now be differentiated precisely from extra-colonic regions. FIG. 7k demonstrates the result of shape-based interpolation, where the CT volume has been interpolated into isotropic resolution to minimize geometric distortions in polyp detection.

Parameter Estimation

For parameter optimization, an anthropomorphic human-colon phantom (Phantom Laboratory, Salem, N.Y., USA) was filled partially with three different concentrations of an iodine-based tagging agent (Oxilan, Guerbet, Bloomington, Ind., USA). The materials of the phantom had been designed to resemble features observed in human CTC scans. In particular, the CT attenuations of soft-tissue structures were 100 HU. The phantom was scanned by use of a four-channel CT scanner (LightSpeed, GE Medical Systems, Milwaukee, Wis., USA) with CT parameters similar to those used routinely with clinical cases at our institution: 3.75 mm collimation, a 1.8 mm reconstruction interval, and a 50 mA current with 140 kVp voltage. The three resulting CT scans represented the phantom with uniform taggings of retained fluid at 300 HU, 600 HU, and 900 HU.

Automated Polyp Detection

The detection of polyps may be based on two volumetric rotation-invariant shape features: a shape index (SI) and a curvedness (CV). The SI characterizes a topologic 3-D shape of a local iso-intensity surface patch in the vicinity of a voxel, and the CV characterizes the flatness of the shape indicated by the SI. Polyp candidates are detected by the application of hysteresis thresholding of the SI and CV features. The complete regions of the detected polyp candidates are extracted by use of conditional morphologic dilation. False positives ("FP") are reduced by applying a Bayesian neural network (BNN), based on shape and texture features calculated from the regions of polyp candidates. The final output of the CAD scheme is determined based on a decision surface generated by the BNN. All of these steps can be fully automated.

Figure 8:
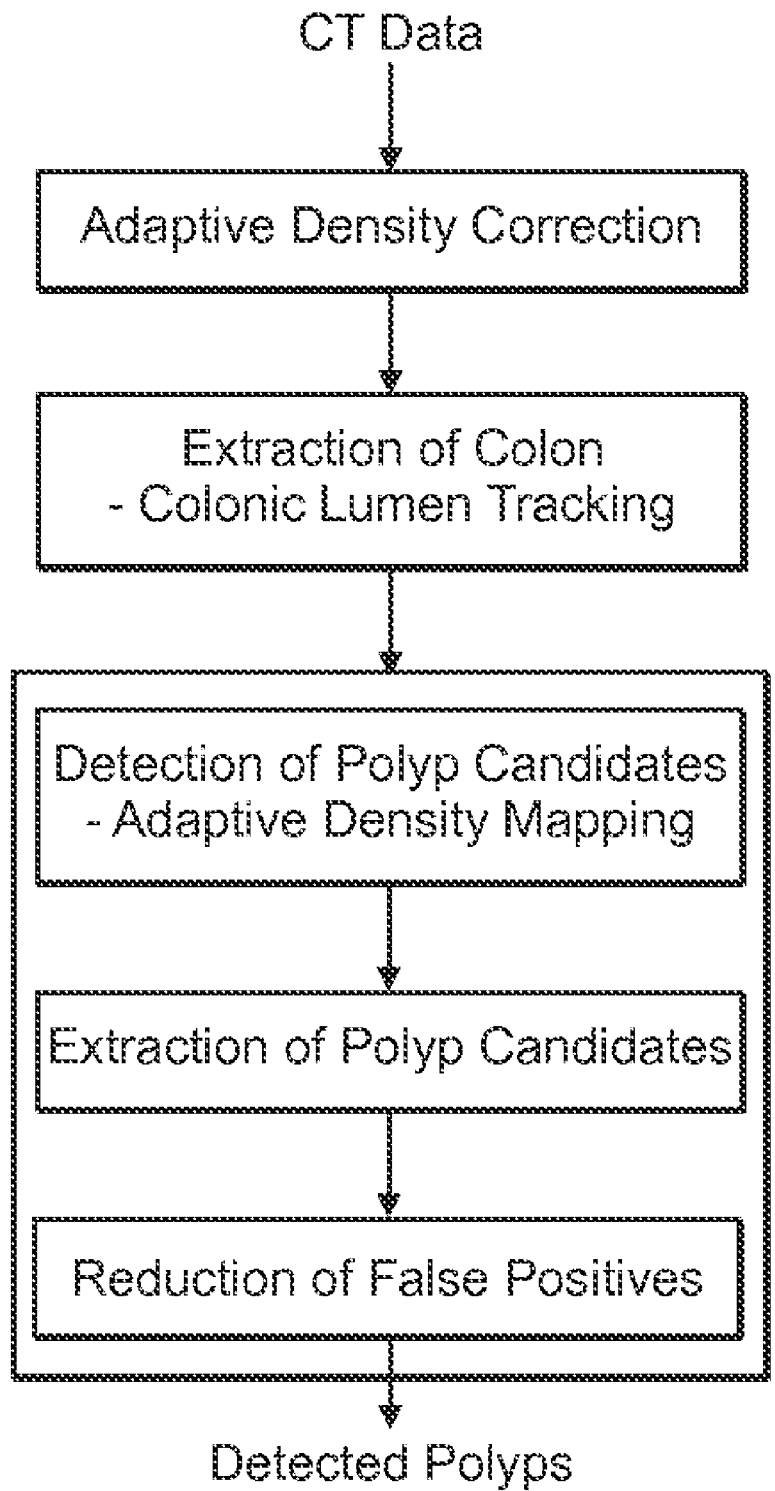
FIG. 8 is a flowchart of one embodiment of an automated polyp detection method, according to one embodiment of the present invention.

ADC, ADM and lumen tracking, or any combination thereof, may be used as preprocessing steps for automatic polyp detection. FIG. 8 is a flowchart of one embodiment of an automated polyp detection method, although the order of colonic extraction and the adaptive density mapping may be reversed. Furthermore, the disclosed methods and systems may be used in combination or separately.

A system for implementing the above-described lumen tracking may be implemented by a computer executing instructions stored in a memory. Input data, such as CT values of voxels in a CT scan of a human being, can be provided from a CT system to the above-described computer, or the above-described computer can be integrated into the CT system. In common practice, CT data is received from a CT system and stored in a picture archiving and communication system (PACS). This data can be used by the above-described computer to perform lumen tracking, such as in a preprocessing step prior to CAD.

Some of the functions performed by the lumen tracking system and method have been described with reference to flowcharts. Those skilled in the art should readily appreciate that functions, operations, decisions, etc. of all or a portion of each block, or a combination of blocks, of the flowcharts can be implemented as computer program instructions, software, hardware, firmware or combinations thereof. Those skilled in the art should also readily appreciate that instructions or programs defining the functions of the present invention can be delivered to a processor in many forms, including, but not limited to, information permanently stored on non-writable storage media (e.g. read only memory devices within a computer, such as ROM, or devices readable by a computer I/O attachment, such as CD-ROM disks), information alterably stored on writable storage media (e.g. floppy disks and hard drives) or information conveyed to a computer through communication media, including computer networks. In addition, while the invention may be embodied in software, the functions necessary to implement the invention may alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Moreover, while the preferred embodiments are described in connection with CT data, one skilled in the art will recognize that the system may be embodied using data from a variety of image systems, such as magnetic resonance imaging (MRI), X-ray, ultrasound and the like. Furthermore, subsets, combinations and subcombinations of the described systems and methods can be used alone or with other systems. Accordingly, the invention should not be viewed as limited, except by the scope and spirit of the appended claims.

What is claimed is:

1. A computer-implemented method for automatically extracting image date for a colon from computed tomographic image data, the method comprising:
    automatically identifying a lumenic structure in the image data, such that the lumenic structure includes an automatically established landmark portion of the colon;
    automatically testing at least one lumenic structure that does not include an automatically established landmark portion of the colon for appropriateness to be appended to the identified lumenic structure; and
    if the tested lumenic structure is appropriate, appending the tested lumenic structure to the identified structure.

2. A method according to claim 1, wherein the included automatically established landmark portion of the colon represents a rectum.

3. A method according to claim 1, wherein the included automatically established landmark portion of the colon represents a descending colon.

4. A method according to claim 1, wherein the included automatically established landmark portion of the colon represents a splenic flexure.

5. A method according to claim 1, wherein the included automatically established landmark portion of the colon represents a hepatic flexure.

6. A method according to claim 1, wherein the included automatically established landmark portion of the colon represents an ascending colon.

7. A method according to claim 1, wherein the included automatically established landmark portion of the colon represents a cecum.

8. A method according to claim 1, wherein the lumenic structure comprises a lumenic path.

9. A method according to claim 1, wherein:
    automatically identifying the lumenic structure comprises automatically identifying a plurality of lumenic structures in the image data, such that each of the automatically identified lumenic structures includes a respective automatically established landmark portion of the colon;
    automatically testing the at least one lumenic structure comprises automatically testing at least one lumenic structure that does not include an automatically established landmark portion of the colon for appropriateness to be appended to at least one of the plurality of identified lumenic structures; and
    appending the tested lumenic structure to the identified structure comprises appending the tested lumenic structure to at least one of the plurality of identified lumenic structures.

10. A method according to claim 9, wherein the lumenic structure comprises a lumenic path.

11. A method according to claim 9, wherein the respective included landmark portions of the colon represent at least two of: a rectum, a descending colon, a splenic flexure, a hepatic flexure, an ascending colon and a cecum.

12. A method according to claim 11, wherein the lumenic structure comprises a lumenic path.

13. A system for automatically extracting image date for a colon from computed tomographic image data, the system comprising:
    a computer system programmed to:
    automatically identify a lumenic structure in the image data, such that the lumenic structure includes an automatically established landmark portion of the colon;
    automatically test at least one lumenic structure that does not include an automatically established landmark portion of the colon for appropriateness to be appended to the identified lumenic structure; and if the tested lumenic structure is appropriate, automatically append the tested lumenic structure to the identified structure.

14. A system according to claim 13, wherein the automatically established landmark portion of the colon represents at least one of: a rectum, a descending colon, a splenic flexure, a hepatic flexure, an ascending colon and a cecum.

15. A system according to claim 13, wherein:

the computer system programmed is programmed to automatically identify the lumenic structure by automatically identifying a plurality of lumenic structures in the image data, such that each of the automatically identified lumenic structures includes a respective automatically established landmark portion of the colon;

the computer system programmed is programmed to automatically test the at least one lumenic structure by automatically testing at least one lumenic structure that does not include an automatically established landmark portion of the colon for appropriateness to be appended to at least one of the plurality of identified lumenic structures; and the computer system programmed is programmed to append the tested lumenic structure to the identified structure by appending the tested lumenic structure to at least one of the plurality of identified lumenic structures.

16. A system according to claim 15, wherein the lumenic structure comprises a lumenic path.

17. A system according to claim 15, wherein the respective included landmark portions of the colon represent at least two of: a rectum, a descending colon, a splenic flexure, a hepatic flexure, an ascending colon and a cecum.

18. A system according to claim 17, wherein the lumenic structure comprises a lumenic path.

19. A tangible computer-readable medium storing a computer program, comprising:

computer instructions to automatically identify a lumenic structure in the image data, such that the lumenic structure includes an automatically established landmark portion of the colon;

computer instructions to automatically test at least one lumenic structure that does not include an automatically established landmark portion of the colon for appropriateness to be appended to the identified lumenic structure; and computer instructions to, if the tested lumenic structure is appropriate, automatically append the tested lumenic structure to the identified structure.

* * * * *